US00PP12932P2

(12) United States Plant Patent
Akerboom

(10) Patent No.: US PP12,932 P2
(45) Date of Patent: Sep. 10, 2002

(54) ASTER PLANT NAMED 'DARK MILKA'

(75) Inventor: Petrus J. Akerboom, Tel Aar (NL)

(73) Assignee: De Nachtvlinder B.V., Ter Aar (NL)

( * ) Notice: Subject to any disclaimer, the term of this patent is extended or adjusted under 35 U.S.C. 154(b) by 0 days.

(21) Appl. No.: 09/263,154

(22) Filed: Mar. 5, 1999

(51) Int. Cl.[7] ..... A01H 5/00

(52) U.S. Cl. ..... Plt./355
(58) Field of Search ..... Plt./355

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Aster plant named 'Dark Milka', characterized by its freely and uniform flowering; decorative inflorescence form with dark purple ray florets; and good post-production longevity.

1 Drawing Sheet

BACKGROUND OF THE INVENTION

The present Invention relates to a new and distinct cultivar of Aster plant, botanically known as *Aster novi-belgii* and referred to by the cultivar name Dark Milka.

The new Aster is a whole plant mutation of the commercial *Aster novi-belgii* cultivar Milka, disclosed in U.S. Plant Pat. No. 10,602. The new Aster was discovered and selected by the Inventor in a controlled environment in Ter Aar, The Netherlands, as a single flowering plant among a population of plants of the parent cultivar Milka in June, 1994. This single plant consistently formed inflorescences having darker purple, 88A to 88B, ray florets compared to the lighter purple, 85A to 85C, ray florets of the cultivar Milka.

Asexual reproduction of the new Aster by terminal cuttings taken at Ter Aar, The Netherlands, has shown that the unique features of this new Aster are stable and reproduced true to type in successive generations.

SUMMARY OF THE INVENTION

The following traits have been repeatedly observed and are determined to be the unique characteristics of 'Dark Milka'. These characteristics in combination distinguish 'Dark Milka' as a new and distinct cultivar:

1. Freely and uniform flowering.
2. Decorative inflorescence form with dark purple ray florets.
3. Good post-production longevity.

Plants of the new Aster can be compared to plants of the sibling cultivar Pink Milka (U.S. Plant patent application Ser. No. 09/263,152). Plants of the new Aster have narrowly elliptic and dark purple, 88A to 88B, ray florets whereas plants of the cultivar Pink Milka have narrowly obovate and light pink, 75C to 75D, ray florets.

Plants of the new Aster can also be compared to plants of the sibling cultivar Karmijn Milka (U.S. Plant patent application Ser. No. 09/263,153). Plants of the new Aster have darker purple ray florets than plants of the cultivar Karmijn Milka, 88A to 88B and 82B, respectively.

The cultivar Dark Milka has not been observed under all possible environmental conditions. The phenotype may vary somewhat with variations in environment such as temperature, daylength and light intensity, without, however, any variance in genotype.

BRIEF DESCRIPTION OF THE PHOTOGRAPH

The accompanying colored photograph illustrates the overall appearance of the new Aster, showing the colors as true as it is reasonably possible to obtain in colored reproductions of this type. Colors in the photograph may differ slightly from the color values cited in the detailed botanical description which accurately describe the colors of the new Aster. The photograph comprises a side perspective view of a typical cut flower stem of the new Aster.

DETAILED BOTANICAL DESCRIPTION

In the following description, color references are made to The Royal Horticultural Society Colour Chart except where general terms of ordinary dictionary significance are used. The aforementioned photographs, following observations and measurements describe plants grown as cut flowers during the summer in Ter Aar, The Netherlands, in a glass-covered greenhouse with average day temperatures of 17 to 35° C. and night temperatures of 14 to 20° C. Plants received long day/short night treatments, 18 hours light, for seven weeks and then were forced into flower with short day/long night treatments, 12 hours light. Plants were about 12.5 to 13 weeks old.

Botanical classification: *Aster novi-belgii* cultivar Dark Milka.

Commercial classification: Cut flower Aster; can also be produced as a potted plant.

Parentage: Whole plant mutation of *Aster novi-belgii* cultivar Milka, disclosed in U.S. Plant Pat. No. 10,602.

Propagation:

*Type.*—Terminal tip cuttings.

*Time to initiate roots.*—About 8 to 10 days at a temperature of 18 to 23° C.

*Time to develop roots.*—Summer: About 16 to 20 days at a temperature of 23° C. Winter: About 20 to 25 days at a temperature of 18° C.

*Root description.*—Fine, fibrous and well-branched.

Plant description:

*Appearance.*—Herbaceous cut flower. Stems upright; medium plant height at flowering. Freely and uniformly flowering; dark purple-colored decorative inflorescences.

*Crop time.*—About 12.5 to 13 weeks from planting to harvest of cut flowering stems.

*Branching habit.*—Freely branching, typically more than 25 lateral branches per plant.

*Growth rate.*—Moderate to slow.

*Plant height.*—About 100 to 110 cm.

*Plant width.*—About 35 cm.

*Lateral branch length.*—At the top of the flowering stem: About 1 mm. At the middle of the flowering stem: About 20 to 29 cm. At the bottom of the flowering stem: About 4 to 12 cm.

*Lateral branch diameter.*—At the top of the flowering stem: About 1.1 mm. At the middle of the flowering stem: About 1.6 to 1.9 mm. At the bottom of the flowering stem: About 2 to 2.4 mm.

*Internode length.*—$5^{th}$ node from apex: About 1.4 to 1.8 cm. $10^{th}$ node from apex: About 1.9 to 2.5 cm. $15^{th}$ node from apex: About 2.1 to 2.7 cm. $20^{th}$ node from apex: About 2 to 3.3 cm.

*Stem color.*—Green, 144A to 146A, no anthocyanin at internodes.

*Stem texture.*—Glabrous or slightly pubescent.

*Foliage description.*—Arrangement: Alternate. Quantity: About 44 to 48 per lateral stem. Shape: Narrowly elliptic; apex acute; base attenuate, sessile; margin serrate. Size: At the top of the flowering stem:: About 1.1 to 1.6 cm in length and about 2 to 2.4 mm in width. At the middle of the flowering stem: About 13.5 to 16 cm in length and about 1.4 to 1.7 mm in width. At the bottom of the flowering stem: About 17.6 to 19.8 cm in length and about 2.1 to 2.3 in width. Texture: Glabrous, leathery. Color: Young leaves, upper surface: 147A. Young leaves, lower surface: Slightly lighter than 137C. Fully expanded leaves, upper surface: 147A. Fully expanded leaves, lower surface: 146B. Venation, upper and lower surfaces: 145C.

Flowering description:

*Appearance.*—Decorative inflorescence form. Inflorescences held on wiry peduncles, arising from leaf axils; inflorescences face upright. Disc and ray florets arranged acropetally on a capitulum.

*Flowering response.*—Under natural conditions, plants flower in the late summer/autumn. At other times of the year, inflorescence initiation and development can be induced under short day/long night conditions. Response time is about 5.5 to 6 weeks.

*Post-production longevity.*—Good, inflorescences last about 3.5 to 4.5 weeks on the plant; about 2 to 3 weeks as a cut flower without postproduction treatments. Inflorescences persistent.

*Quantity of inflorescences.*—Inflorescences form at every leaf axil. Freely flowering, usually about 52 to 84 inflorescences per flowering stem.

*Fragrance.*—None.

*Inflorescence size.*—Diameter: About 3.2 cm. Depth (height): About 1 to 1.4 cm. Disc diameter: About 7 mm.

*Inflorescence bud.*—Shape: Cylindrical. Length: About 7 to 8 mm. Diameter: About 7 to 8 mm. Color: 137B.

*Ray florets.*—Quantity of ray florets per inflorescence: About 296. Shape: Narrowly elliptic; apex rounded; base attenuate; margin entire. Length: About 1.2 to 1.3 cm. Width: About 1.3 to 2 mm. Texture: Satiny, smooth and glabrous. Color: When opening, upper surface: 88A. When opening, lower surface: 88B. Mature, upper surface: 88A to 88B; fading to 88C to 85A. Mature, lower surface: 88C.

*Disc florets.*—Quantity: About 157 inflorescence. Shape: Tubular. Length: About 7 mm. Diameter: At apex, about 2 mm; at base, about 1 mm. Color: Immature: 154A. Mature: 9A to 9B.

*Peduncle.*—Strength: Strong. Length: Apical peduncle: About 4 to 6 mm. Fourth peduncle: About 2 to 3 mm. Seventh peduncle: About 2 mm. Color: 146A to 147A.

*Reproductive organs.*—Androecium: Not present on ray florets. Gynoecium: Pistil length: About 3.5 to 4.5 mm. Stigma color: Yellow, 10C to 10D. Style length: About 2 mm.

*Seed development.*—Not observed.

Disease resistance: Plants of the new Aster have not been observed to be resistant to pathogens common to Asters, however plants of the new Aster appear to be less sensitive to Powdery Mildew than other known cultivars of Aster.

It is claimed:

1. A new and distinct cultivar of Aster plant named 'Dark Milka', as illustrated and described.

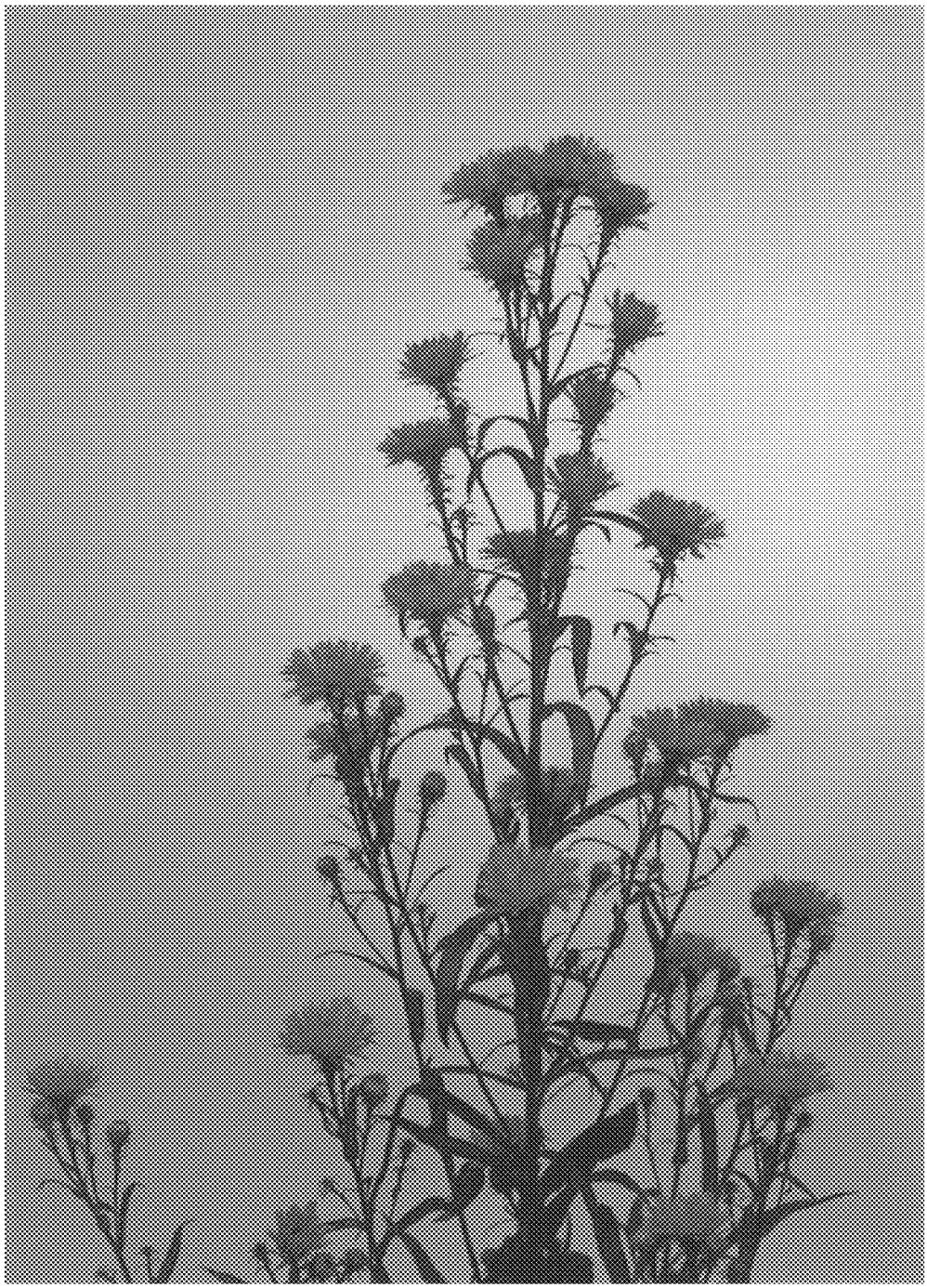

* * * * *